US006803059B2

(12) United States Patent
Lu

(10) Patent No.: US 6,803,059 B2
(45) Date of Patent: Oct. 12, 2004

(54) **ANTI-TUMOR METALLOCOMPLEXES OF CRUDE EXTRACTS FROM *CANAVALIA ENSIFORMIS***

(75) Inventor: Sou-Yi Lu, Panchiao (TW)

(73) Assignee: Jim Lu, Gaithersburg, MD (US)

( * ) Notice: Subject to any disclaimer, the term of this patent is extended or adjusted under 35 U.S.C. 154(b) by 23 days.

(21) Appl. No.: 10/302,643

(22) Filed: Nov. 21, 2002

(65) Prior Publication Data

US 2004/0101585 A1 May 27, 2004

(51) Int. Cl.$^7$ ............... A01N 65/00; A61K 9/50; A61K 35/78; C07K 16/00

(52) U.S. Cl. ............ 424/757; 424/499; 424/776; 530/370; 530/379; 530/389.7; 530/391.5

(58) Field of Search ................. 530/378, 389.7, 530/391.5, 370; 424/499, 195.1

(56) References Cited

PUBLICATIONS

Pan J. et al. Inhibition of Cell Growth Caused by Aluminum Toxicity Rsults from Auminum–Iduced Cell Death in Breley Supension Cells, J. Plant Nutrition, 2002.*
El–Rahman S. Neuropathology of aluminum toxicity in rats (glutamate and GABA impairment), Pharmacological Reserch, 2003, 47, 189–194.*
Obata F. et al. Preparation of Concanavalin A Consisting Solely of Intact Subunits, J. Biochem., 1978, 84, 103–109.*
Obata F. et al. Concanavalin A Binds Various Numbers of Calcium and Manganese Ions, J. Biochem. 1979, 85, 1037–1045.*

* cited by examiner

Primary Examiner—Rebecca E. Prout
Assistant Examiner—Malgorzata A. Walicka

(57) ABSTRACT

An anti-tumor pharmaceutical composition comprises the conjugation of *Canavalia ensiformis*-extracted protein with metal ions to form a metalloprotein complex for inhibiting the growth of tumor with enhanced activity and stability, but without toxicity.

5 Claims, 3 Drawing Sheets

ANTI-TUMOR METALLOCOMPLEXES OF CRUDE EXTRACTS FROM *CANAVALIA ENSIFORMIS*

BACKGROUND OF THE INVENTION

There are many ways for treating cancer. Besides the surgery to remove malignant tumor for treating cancer, a chemotherapy or radiation therapy may be applied for the treatment of cancer. However, it will incur side effects to hurt the patient.

It is known that many compositions are derived from Chinese herbal medicines, medicinal plants and extracts thereof for treating cancers. Nevertheless, a single plant extract without being conjugated with other effective ingredients, its anti-tumor effect is still unsatisfactory.

The present inventor has found these phenomena and invented the present anti-tumor composition by conjugating *Canavalia ensiformis*-extracted protein with metal ions.

SUMMARY OF THE INVENTION

The object of the present invention is to provide an anti-tumor pharmaceutical composition comprising the conjugation of *Canavalia ensiformis*-extracted protein with metal ions to form a metalloprotein complex for inhibiting the growth of tumor with enhanced activity and stability, but without toxicity.

DETAILED DESCRIPTION

Figure 1:
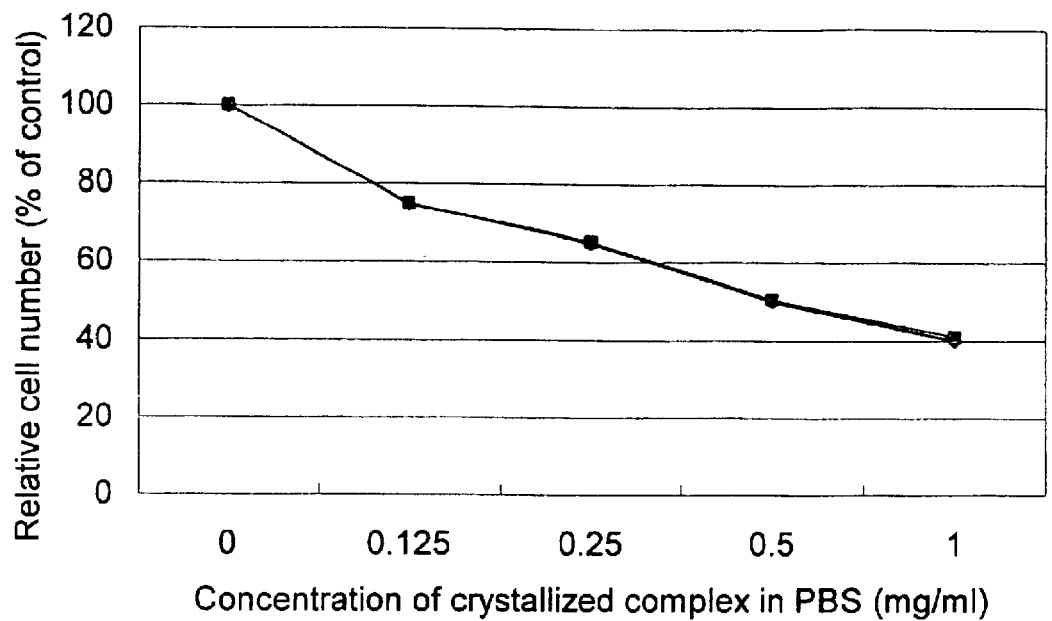
FIG. 1 shows a SW-480 cell proliferation assay, in which the ordinate indicates cell number as percent of control, and the abscissa indicating the concentration of crystallized complex (mg/ml); IC 50: 0.375 mg/ml.

For preparing the anti-tumor pharmaceutical composition of the present invention, the following steps of the preparation procedure may be applied:

A. Pre-treatment of *Canavalia ensiformis* Seeds:
  1. Fresh seeds of *Canavalia ensiformis* as planted in Taiwan, 10 grams, are obtained for water-washing, soaking in the water and drying in the air.
  2. The dried seeds were then ground into fine powder and lipids were extracted with 100 ml of hexane for 10 minutes. The solvent is then decanted and the precipitate is collected for next treatment.
  3. The precipitate is then dissolved in 100 ml of pure water (pH: 7) and stirred for 30 minutes at the temperature ranging from 0° C. to room temperature to obtain an aqueous solution containing the *Canavalia ensiformis* protein.

B. Formation of Metalloprotein Complex:
  1. The aqueous solution is settled for 30~60 minutes to precipitate any impurity residue which is then removed. Such an aqueous solution is then filtered to remove any residue through a filtration membrane, e.g., 0.22 μm milipore membrane to obtain a crude solution of *Canavalia ensiformis*-extracted protein from the filtrate.
  2. Magnesium oxide (MgO), or calcium chloride ($CaCl_2$) or aluminum hydroxide ($Al(OH)_3$) were mixed with the solution of crude water extract of *Canavalia ensiformis* protein under agitation for four hours to obtain the metalloprotein complex solution. Pure water was added to adjust protein concentration to 1 mg protein/1 ml of metallocomplex solution for oral administration. MgO. $CaCl_2$ and $Al(OH)_3$ can also be used when mixed in a weight ratio 1:1:1.

Such group of metallic-ion containing compounds include metallic ions of aluminum ion ($Al^{+++}$), magnesium ion ($Mg^{++}$) and calcium ion ($Ca^{++}$). When mixing the metallic-ion containing compounds (of which the weight may be designated as Wi) with the crude solution of *Canavalia ensiformis*-extracted protein (of which the weight may be designated as Wp) for making the complex solution, the following mixing ratio may be considered:

$$Wi:Wp=1:50$$

3. The metalloprotein complex solution is lyophilized by a lyophilizer to obtain crystallized complex. An excipient such as lactose may be added into the crystallized complex with a weight ratio of 3:1, i.e., 3 parts of excipient with one part of crystallized complex, thereby producing pharmaceutically acceptable powder, tablets and capsules of the *Canavalia ensiformis*-extracted protein conjugated with metal ions.

Conjugating the *Canavalia ensiformis* extract with metallic ions increases the activity and stability of the crude extract.

When the conjugate (pH>7) of this invention passing through the stomach filled with gastric acid into the intestinal canal, the metallic ions will render an active transport in cooperation with the excipient or carrier (such as lactose) to thereby increase the absorptivity of the effective ingredients of the present invention by the patient's body (e.g. the villi) to greatly inhibit the tumor growth for enhancing the anti-tumor effect.

Besides the excipient of lactose, other protein carriers such as the protein carrier existing in milk or other natural foods may be served for an effective "carrier" for carrying the effective ingredients of the present invention to the patient's target organs or cells for treating his or her cancer.

Although the metallic-ion compounds containing group ions of aluminum, magnesium and calcium ions as above-mentioned may be together conjugated with the *Canavalia ensiformis* extracted protein to effectively treat a patient's tumor, other metallic-ion compound containing single ion (without forming group of ions or plural ions) may also be conjugated with the extracted protein, not limited in this invention.

The above-mentioned examples are given for describing the present invention only, but not to limit the claiming scope of this application within the examples as described herewith. If merely feeding natural beans of *Canavalia ensiformis*, no anti-tumor effect has been proven.

In order to prove the medicinal effect of the present invention, a plurality of tests are performed and reported as follows:

In Vitro Test:

Four different cancer cells as listed below are respectively tested for checking their proliferation by adding therein with the aqueous solution of the crystallized complex of the present invention:
a. Cells from a primary adenocarcinoma of the human colon, SW-480 according to ATCC of USA;
b. Cells from human bladder cancer, TSGH-8301;
c. Cells from mammary gland, breast adenocarcinoma MCF-7 (ATCC, USA); and
d. Cells from Lewis lung carcinoma, LLC (ATCC, USA).

EXAMPLE 1

Five tubes are provided each filled with 1 ml of aqueous solution of crystallized complex of the present invention and their concentrations have been adjusted for five groups as follows:
(1) original-concentration solution: 1 mg crystallized complex/1 ml solution;
(2) diluted solution by adding 1 ml phosphate buffer solution (PBS) into original-concentration solution: 0.5 mg complex/ml;
(3) diluted solution (added with 3 ml PBS): 0.25 mg/ml;
(4) diluted solution (added with 5 ml PBS): 0.125 mg/ml;
(5) diluted solution (added with 7 ml PBS): 0.0625 mg/ml.

The SW-480 (colon cancer) cells, with cell number of $1 \times 10^4$ cell/ml, are transferred by pipet into wells of several well plates. Each well is then added therein with the above-prepared aqueous solution of crystallized complex of different concentrations, i.e., 1 mg/1 ml, 0.5 mg/ml, 0.25 mg/ml, 0.125 mg/ml and 0.0625 mg/ml respectively for incubation of the cancer cells. After 3 days, each group of the aqueous solution is analyzed by adding crystalviolet (0.1%) therein and by an analysis instrument such as ELISA reader to obtain the test result as shown in FIG. 1, from which the solution with increased concentration of the crystallized complex of the present invention results in a smaller cell number, thereby proving the tumor-inhibition effect of the present invention.

EXAMPLE 2

Figure 2:
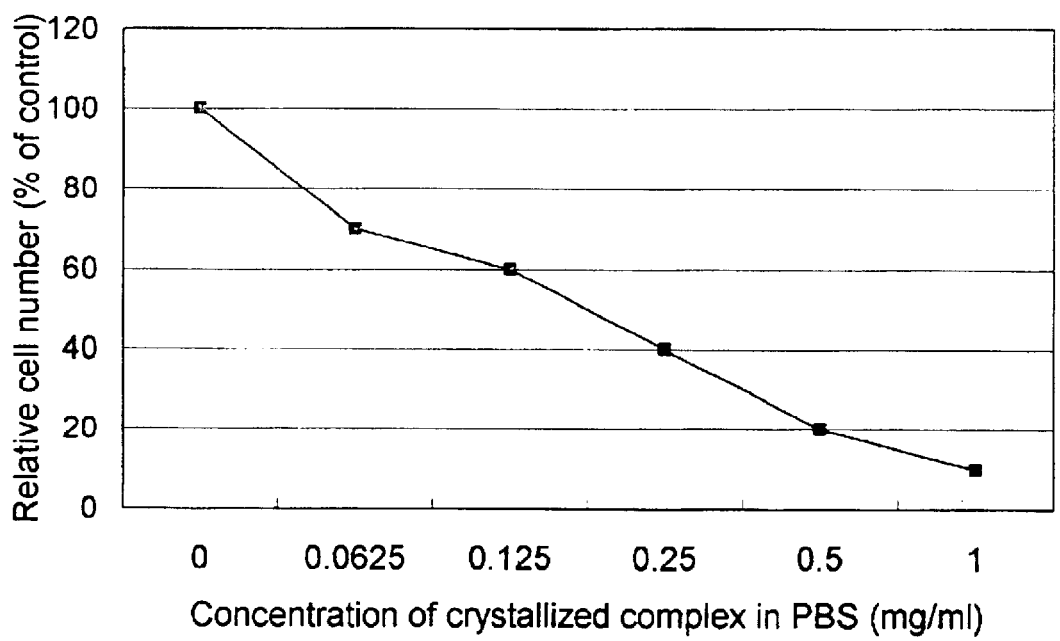
FIG. 2 shows a TSGH cell proliferation assay, in which the ordinate indicates cell number as percent of control, and the abscissa indicating the concentration of crystallized complex (mg/ml); IC 50: 0.1875 mg/ml.

The testing procedures of Example 1 are repeated by checking the cells of TSGH-8301 (bladder cancer) to obtain the test result as shown in FIG. 2.

EXAMPLE 3

Figure 3:
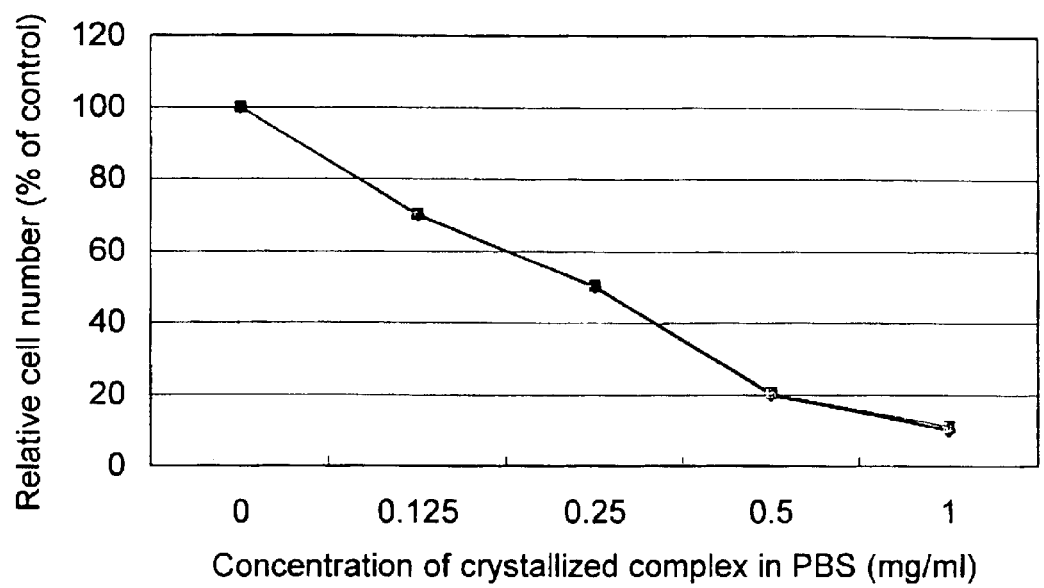
FIG. 3 shows a MCF-7 cell proliferation assay, in which the ordinate indicates cell number as percent of control, and the abscissa indicating the concentration of crystallized complex (mg/ml); IC 50: 0.25 mg/ml.

Testing procedures of Example 1 are repeated, but cells of MCF-7 (breast cancer) are tested to obtain the result as shown in FIG. 3.

EXAMPLE 4

Figure 4:
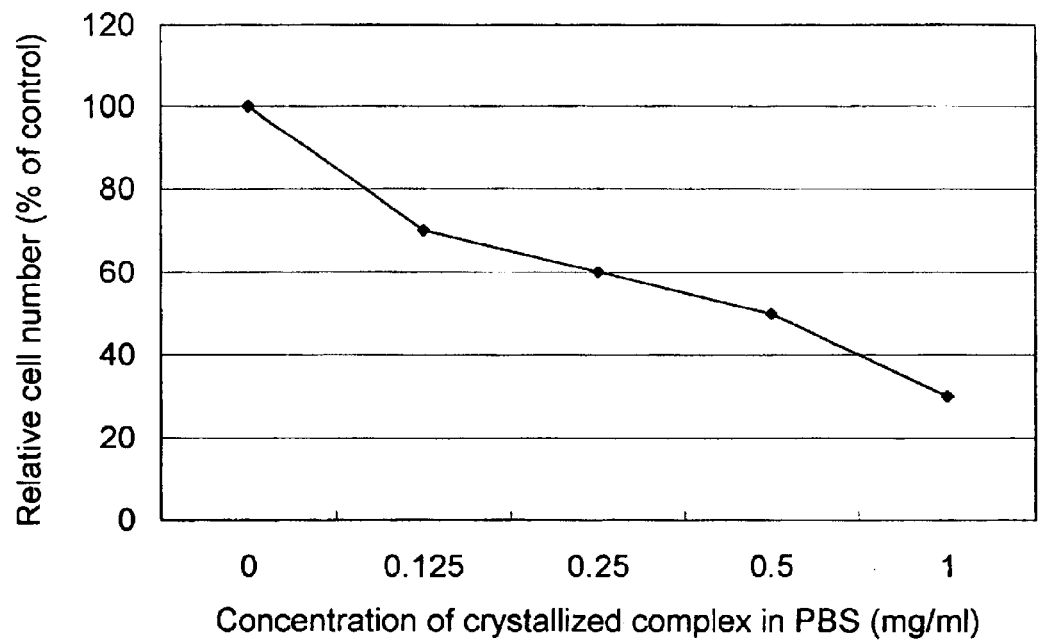
FIG. 4 shows a LLC cell proliferation assay, in which the ordinate indicates cell number as percent of control, and the abscissa indicating the concentration of crystallized complex (mg/ml); IC 50: 0.5 mg/ml.

Example 1 is repeated, except that the LLC (lung cancer) cells are tested to have the result as shown in FIG. 4.

Anti-Tumor Animal Module:
B6-mice are divided into three groups, 10 mice for each group (5 male and 5 female) to be tested as follows:
Each mouse ready for test has an average weight of 20 grams.
1. Control group: each B6 mouse fed with PBS 2 ml every day.
2. Low dose group: each B6 mouse fed with 10 mg crystallized complex in 2 ml PBS every day.
3. High dose group: each B6 mouse fed with 40 mg crystallized complex in 2 ml PBS every day.
Injection with Lewis Lung Carcinoma cell: $4 \times 10^6$/ml
After feeding Group 1, 2, 3 from the first day through the 35th day, the respective tumor size and weight of mice are observed as follows:

a. Average Weight (g):

There is showing no appreciable weight variation even fed with high dose.

|  | control | low dose group | high dose group |
|---|---|---|---|
| 1st day | 19.5 | 20 | 18.6 |
| 7th day | 19 | 17 | 18.5 |
| 14th day | 20.1 | 20.5 | 20.1 |
| 21st day | 20.4 | 21.1 | 20.3 |
| 28th day | 20.3 | 20.8 | 20.1 |
| 35th day | 20.2 | 21.0 | 20.4 | b. Average Tumor Size ($mm^3$):

|  | control | low dose group | high dose group |
|---|---|---|---|
| 1st day | 0 | 0 | 0 |
| 7th day | 90 | 44 | 30 |
| 14th day | 190 | 107 | 57 |
| 21st day | 539 | 388 | 190 |
| 28th day | 880 | 577 | 208 |
| 35th day | 1545 | 685 | 188 |

Figure 5:
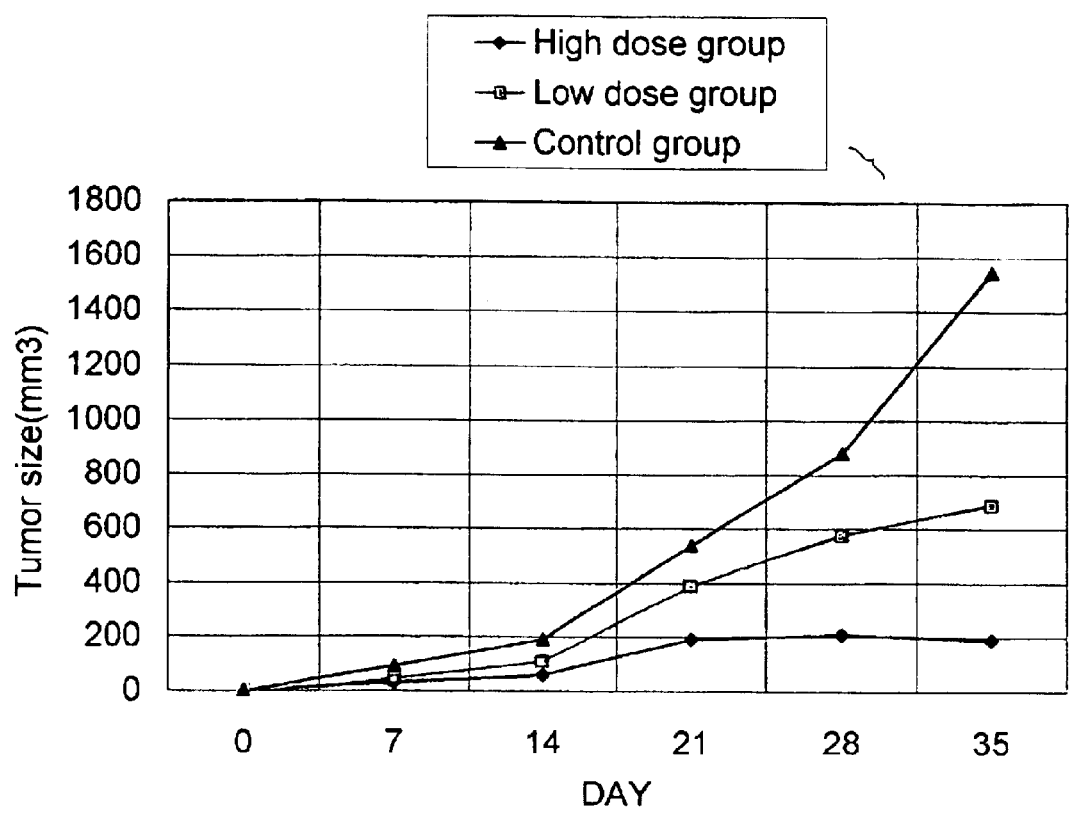
FIG. 5 shows relationship between the tumor size and time for untreated and treated animals.

The tumor size vs. days after dosage is shown in FIG. 5. Especially reviewing the high dose curve (with logenze dots), the period after 21 days through 28 days and 35 days indicates a flat (not sharp upwardly) growth rate, proving the remarkable tumor inhibition as effected by the present invention.

Toxicity Test 10 rats (5 male, 5 female) average 200–250 g for each rat, 8 rats fed with 4 g crystallized complex in 4 ml normal saline, 2 rats fed with 4 ml normal saline as control group.

Observation of survival, changes in hair, skin, weight, and toxicity syndrome, proved that administrtion of the composition of the present invention has no toxic effects. Table 1 shows the result.

TABLE 1

| | WBC ($\times 10^3/\mu l$) | RBC ($\times 10^6/\mu l$) | Hb (g/dl) | platelet ($\times 10^3/\mu l$) | hair & skin | weight (g) | Toxic syndrome |
|---|---|---|---|---|---|---|---|
| Rat No (1) the 1st day | | | | | | | |
| Average | 4.25 | 8.68 | 11.15 | 646.3 | Normal | 235 | None |
| Control group average | 4.65 | 6 | 12.45 | 542 | Normal | 235.5 | None |

TABLE 1-continued

|  | WBC (×10³/μl) | RBC (×10⁶/μl) | Hb (g/dl) | platelet (×10³/μl) | hair & skin | weight (g) | Toxic syndrome |
|---|---|---|---|---|---|---|---|
| (2) the 14th day | | | | | | | |
| Average | 4.85 | 6.3 | 12.1 | 786.6 | Normal | 239 | None |
| Control group average | 4.85 | 6.15 | 17.45 | 675 | Normal | 235 | None |
| (3) the 28th day | | | | | | | |
| Average | 5.75 | 6.5 | 12.3 | 637.5 | Normal | 240 | None |
| Control group average | 4.5 | 6.3 | 15.25 | 516 | Normal | 235.5 | None |
| (4) the 90th day | | | | | | | |
| Average | 6.24 | 6.59 | 11.71 | 665.12 | Normal | 242.6 | None |
| Control group average | 4.35 | 6.55 | 14.75 | 485.5 | Normal | 235.5 | None |

Accordingly, the present invention has shown its effect for inhibiting tumor, but without any toxicity.

The present invention is prepared from a plant extract for treating cancer, causing no side effect as commonly resulted from chemotherapy or radiation therapy.

The present invention may be modified without departing from the spirit and scope of the present invention.

The basic composition may be optionally adjusted for obtaining a proper conjugating proportion range as follows:

| *Canavalia ensiformis* extracted protein | 60~98% (by weight); |
|---|---|
| Metallic-ion containing compound | 2~10% (by weight). |

Other excipients or carriers may be further added into the basic composition as above-mentioned.

I claim:

1. A process for making an anti-tumor composition comprising the steps of:
   a. water-washing of seeds of *Canavalia ensiformis*, soaking the seeds in water and drying the seeds in air;
   b. grinding the seeds into fine powder, extracting the lipids with 100 ml of hexane for 10 minutes and decanting the supernatant;
   c. dissolving the powder in 100 ml distilled water at 0° C. to room temperature, with agitation to obtain an aqueous solution of protein;
   d. allowing for precipitation of undissolved powder for 30–60 minutes and filtering the aqueous solution through a 0.22 μm milipore membrane to obtain a solution of crude extract of protein from *Canavalia ensiformis* seeds;
   e. conjugating the filtered crude solution of *Canavalia ensiformis* protein extracted from seeds with magnesium oxide, calcium chloride, or a 1:1 mixture thereof, wherein the weight ratio of protein and metallic compound is about 50:1 to form a metalloprotein complex solution, and adjusting the protein concentration of the complex to 1 mg protein per 1 ml metalloprotein complex by adding distilled water; and
   f. crystallizing the metalloprotein complex to obtain an anti-tumor composition.

2. An antitumor composition obtained by the process of claim 1.

3. A composition according to claim 2, wherein an excipient and carrier are added to said metalloprotein complex.

4. A composition according to claim 3, wherein said excipient is lactose.

5. A composition according to claim 3, wherein said carrier is a protein carrier.

* * * * *